United States Patent
Rubsamen et al.

(10) Patent No.: US 10,172,936 B2
(45) Date of Patent: *Jan. 8, 2019

(54) PEPTIDE PARTICLE FORMULATION

(71) Applicant: FLOW PHARMA, INC., East Palo Alto, CA (US)

(72) Inventors: Reid M. Rubsamen, Alamo, CA (US); David Earl Heckerman, Santa Monica, CA (US)

(73) Assignee: FLOW PHARMA, INC., East Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/215,336

(22) Filed: Jul. 20, 2016

(65) Prior Publication Data

US 2016/0324956 A1    Nov. 10, 2016

Related U.S. Application Data

(63) Continuation of application No. 13/153,826, filed on Jun. 6, 2011, now Pat. No. 9,408,906.

(60) Provisional application No. 61/351,672, filed on Jun. 4, 2010, provisional application No. 61/354,632, filed on Jun. 14, 2010, provisional application No. 61/372,413, filed on Aug. 10, 2010.

(51) Int. Cl.
| | |
|---|---|
| *A61K 39/385* | (2006.01) |
| *A61K 9/16* | (2006.01) |
| *A61K 39/39* | (2006.01) |
| *A61K 9/51* | (2006.01) |
| *A61K 39/245* | (2006.01) |
| *C12N 7/00* | (2006.01) |
| *A61K 39/00* | (2006.01) |

(52) U.S. Cl.
CPC .......... *A61K 39/385* (2013.01); *A61K 9/1647* (2013.01); *A61K 9/5153* (2013.01); *A61K 39/245* (2013.01); *A61K 39/39* (2013.01); *C12N 7/00* (2013.01); *A61K 2039/55511* (2013.01); *A61K 2039/55555* (2013.01); *A61K 2039/55572* (2013.01); *A61K 2039/57* (2013.01); *A61K 2039/6093* (2013.01); *A61K 2039/70* (2013.01); *C12N 2710/16134* (2013.01)

(58) Field of Classification Search
CPC .. A61K 39/385; A61K 9/1647; A61K 9/5153; A61K 39/245; A61K 39/39; A61K 2039/55511; A61K 2039/55555; A61K 2039/55572; A61K 2039/57; A61K 2039/6093; A61K 2039/70; C12N 7/00; C12N 2710/16134

See application file for complete search history.

(56) References Cited

U.S. PATENT DOCUMENTS

| | | | |
|---|---|---|---|
| 6,596,278 B2 | 7/2003 | Gander et al. | |
| 2004/0142887 A1* | 7/2004 | Cui | A61K 39/0006 514/44 R |
| 2004/0202680 A1* | 10/2004 | O'Hagan | A61K 9/1647 424/277.1 |
| 2007/0122487 A1 | 5/2007 | Deluca et al. | |
| 2008/0260780 A1 | 10/2008 | Cerundolo et al. | |
| 2009/0269362 A1 | 10/2009 | Sant | |
| 2010/0119535 A1 | 5/2010 | Felgner et al. | |
| 2011/0236484 A1* | 9/2011 | Whittum-Hudson | A61K 39/118 424/484 |

FOREIGN PATENT DOCUMENTS

WO    WO 2007/089870    8/2007

OTHER PUBLICATIONS

Ulrich et al., "Monophosphoryl Lipid A as an Adjuvant," in Vaccine Design: The Subunit and Adjuvant Approach, edited by Powell and Newmann, Plenum Press, New York, 1995.*
Dumortier et al, J. Immunol. 2005:855-863.*
Gomez et al., Journal of Controlled Release 130 (2008) 161-167.*
Espuelas et al., Immunologia, 24(2):208-223 (2005).*
Slingluff et al, Cancer Res; 19(15); 4228-38. (2013).*
Ying et al., "Induction of sustained and elevated immune responses to weakly immunogenic synthetic malarial peptides by encapsulation in biodegradable polymer microspheres" Vaccine (Oct. 1, 1996) 14(15):1442-1450.
Bhat Ajaz et al., "Induction of cell-mediated immune responses to peptide antigens of P. vivas in microparticles using intranasal immunization" Immunological Investigations (May 11, 2010) 39:4-5.
Boehm Grard et al., On technological and immunological benefits of multivalent single-injection microsphere vaccines Pharmaceutical Research, Kluwar Academic Publishers, New York, NY, US (Sep. 1, 2002) 19(9)1330-1336 (Abstract Only).
Celis, Esteban, "Getting peptide vaccines to work: just a matter of quality control?" J. Clin.Invest. (Dec. 2002) 110(12):1765-1768.

(Continued)

*Primary Examiner* — Karlheinz R. Skowronek
*Assistant Examiner* — Joseph Fischer
(74) *Attorney, Agent, or Firm* — Karl Bozicevic; Bozicevic, Field & Francis LLP

(57) ABSTRACT

A composition as disclosed is comprised of a plurality of groups of particles. The particles are comprised of a biocompatible polymer which may be a co-polymer such as PLGA combined with a peptide of a sequence of interest, e.g. a sequence which corresponds to a sequence presented on a surface of a cell infected with a virus. A plurality of different groups of particles are provided in the formulation wherein the particles within any single group include peptides of identical amino acid sequence. The particles are sized such that they are sufficiently large so as to prevent more than the contents of a single particle from being presented to a single immune system cell.

20 Claims, 2 Drawing Sheets

(56) References Cited

OTHER PUBLICATIONS

Frangione-Beebe et al., "Microencapsulation of a synthetic peptide epitope for HTLV-1 in biodegradable poly(D,L-lactide-co-glycolide) microspheres using a novel encapsulation technique" J. Microencapsulation (2001) 18(5):663-677.

Jiang et al., "Biodegradable poly(lactic-co-glycolic acid) microparticles for injectable delivery of vaccine antigens" Advanced Drug Delivery Reviews (2005) 57:391-410.

Kim et al., "Microspheres for Drug Delivery" BioMEMS and Biomedical Technology (2006) vol. 1, XXII, 522, p. 19-50 (online: retrieved Jul. 25, 2012), Retrieved from www.springerlink.com/content/w00h56453p362227/.

Lamalle-Bernard D. et al., "Coadsorption of HIV-1 p24 and gp120 proteins to surfactant-free anionic PLA nanoparticles preserves antigenicity and immunogenicity" Journal of Controlled Release, Elsevier, Amsterdam, NL (Sep. 28, 2006) 115(1):57-67.

Mundargi et al., "Nano/micro technologies for delivering macromolecular therapeutics using poly(d,l-lactide-co-glycolide) and its derivatives" Journal of Controlled Release, Elsevier, Amsterdam, NL (Oct. 22, 2007) 125(3):193-209.

Tabata et al., "Size effect on systemic and mucosal immune responses induced by oral administration of biodegradable microspheres" Vaccine (1996) 14(17/18)1677-1685.

Ma et al., "Enhanced presentation of MHC class Ia, Ib and class II-restricted peptides encapsulated in biodegradable nanoparticles: a promising strategy for tumor immunotherapy" Journal of Translational Medicine (2011) 9:34 (pp. 1-10).

Philip J. Norris et al.: "Fine Specificity and Cross-Clade Reactivity of HIV Type 1 Gag-Specific CD4 + T Cells", Aids Research and Human Retroviruses, vol. 20, No. 3, Mar. 1, 2004 (Mar. 1, 2004), pp. 315-325.

Rodriguez et al., "Immunodominance in Virus-Induced CD8+ T-Cell Responses Is Dramatically Modified by DNA Immunization and Is Regulated by Gamma Interferon" Journal of Virology (May 2002) 76(9):4251-4259.

Yu et al., "Consistent Patterns in the Development and Immunodominance of Human Immunodeficiency Virus Type I (HIV-1)-Specific CD8+ T-Cell Responses following Acute HIV-1 Infection" Journal of Virology (Sep. 2002) 76(17):8690-8701.

\* cited by examiner

Figure 1

| | | |
|---|---|---|
| 1A | | Two human dendrocytes each in proximity of three 10 micron PLGA microspheres. |
| 1B | | First dendrocyte phagocytizing three 10 micron PLGA microspheres.<br><br>Second dendrocyte beginning phagocytosis. |
| 1C | | First dendrocyte completing phagocytosis of three 10 micron PLGA microspheres.<br><br>Second dendrocyte in active phagocytosis. |
| 1D | | Second dendrocyte has completed phagocytosis of three 10 micron PLGA microspheres. |

Figure 2
| | | |
|---|---|---|
| 2A | 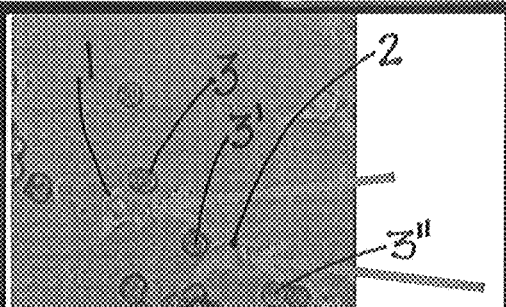 | Two human dendrocytes each in proximity of a 15 micron PLGA microsphere. |
| 2B | 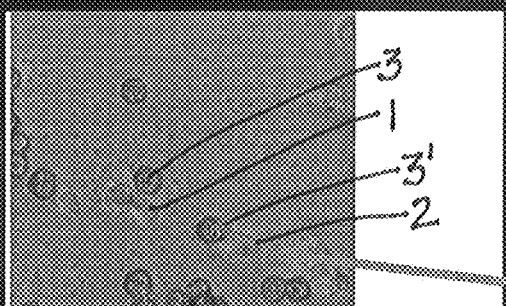 | First dendrocyte phagocytizing a 15 micron PLGA microsphere. |
| 2C | 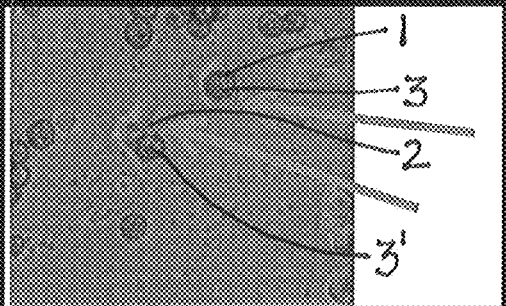 | First dendrocyte completing phagocytosis of one 15 micron PLGA microsphere.<br><br>Second dendrocyte in active phagocytosis. |
| 2D | 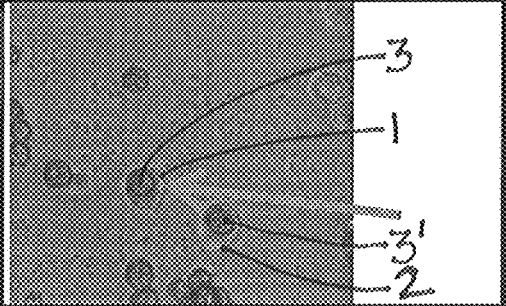 | Second dendrocyte has completed phagocytosis of one 15 micron PLGA microsphere. |

PEPTIDE PARTICLE FORMULATION

FIELD OF THE INVENTION

This invention relates generally to the field of peptide particles which form formulations comprised of groups of particles. The particles of a single group of particles consist only of the same compound, such as a single peptide species.

BACKGROUND OF THE INVENTION

The term vaccine derives from Edward Jenner's 1796 use of the term cow pox (Latin variolae vaccinae, adapted from the Latin vaccīn-us, from vacca cow), which, when administered to humans, provided them protection against smallpox.

The 20th century saw the introduction of several successful vaccines, including those against diphtheria, measles, mumps, and rubella. Major achievements included the development of the polio vaccine in the 1950s and the eradication of smallpox during the 1960s and 1970s. Maurice Hilleman was the most prolific of the developers of the vaccines in the twentieth century. As vaccines became more common, many people began taking them for granted. However, vaccines remain elusive for many important diseases, including malaria and HIV. Vaccines may be dead or inactivated organisms or purified products derived from them.

There are several types of vaccines currently in use. These represent different strategies used to try to reduce risk of illness, while retaining the ability to induce a beneficial immune response. Considerable efforts have been made to develop an HIV vaccine.

A cell infected with HIV virus has many distinct epitopes on its surface. Each epitope can be targeted by the cellular immune response mediated by T-lymphocytes. These T-lymphocytes become sensitized to specific epitopes by exposure to antigens brought to the T-cells by antigen presenting cells (e.g macrophages).

HIV vaccines have been developed to direct cellular immunity mechanisms toward a blood borne HIV virus by sensitizing T-cells, via antigen presenting cells (APCs) exposed to the vaccine, to suites of epitopes on the surface of cells infected with the virus.

Vectors used to introduce vaccines into the cellular immunity pathways have included adenovirus vectors. A problem with traditional vaccine approaches to treating patients already infected with HIV has been the fact that adenovirus vectors tend to activate $CD4^+$ T-cells which in turn can potentially make pre-existing HIV infection more virulent. Another problem with HIV vaccine designs, in general, has been that the end result is to target large suites of epitopes on the surface of the cells infected with the virus, possibly targeting epitopes which could actually worsen various pathological aspects of the HIV infection.

Until recently, little was known about the specific effect of targeting specific epitopes on the surface of cells infected with the HIV virus. Each time a vaccine vector is given to a person with HIV disease, a number of epitopes are targeted, and a number of immune response parameters are measured. Associating a specific response with a specific epitope has been essentially impossible from an analysis of a single vaccine administration. Data from the administration of multiple vaccines to multiple sets of HIV infected subjects with corresponding cellular immune responses could, in theory, allow the effects of the individual epitopes to be de-convolved, essentially through a very computational intensive cross-correlation exercise.

Recent work in the field has brought modern supercomputer technology to bear on this problem, resulting in a list of putative individual pathogen-relevant effects of individual epitopes on the surface of cells infected with the HIV virus.

Results from immunization with antigen-containing PLGA microspheres made from a double-emulsion process utilizing organic solvents have been mixed, however, perhaps owing to the fact that the solvent systems and shear forces used in such microsphere fabrication processes can cause protein conformational changes that may interfere with the antigen-presenting event.

Peptides injected into the lymphatic system can be taken up by APCs, thereby producing an immune response. If a single APC takes up more than one antigen and simultaneously presents multiple antigens to T-cells, this may result in a cellular immune response wherein the response is targeted to only one of the antigens that was presented.

Methods for relieving the effects of immunodominance are described in published US patent application 20080260780, entitled "Materials And Methods Relating To Improved Vaccination Strategies"; US patent application 20090269362, entitled "Method for Controlling Immunodominance"; and US patent application 20100119535, entitled "Compositions and Methods for Immunodominant Antigens."

SUMMARY OF THE INVENTION

A composition is disclosed which is comprised of a plurality of groups of particles, which may be substantially spherical particles, comprised of a polymer and an antigen, e.g. a peptide, lipid, glycolipid, phospholipid, polysaccharide, etc. All of the particles in all of the groups have a narrow particle size range of about 10 µm±20% to about 20 µm±20% in diameter. The size range can be such that only a single particle can be consumed by an antigen presenting cell, by which is usually intended a professional antigen presenting cell. For example, the particle size may be in a range of 12 microns to 18 microns in diameter. The particles sizes may be 15 microns in diameter±20%. The size of the particles on a given formulation may be substantially the same size, i.e. ±20% or ±10%, ±2%, or ±1% in diameter.

Each particle comprises one or more antigenic compounds, including without limitation peptides, where the compounds in a particle are of identical species or sequence. When peptides are used they are generally small and should be at least 8 and not more than 20 amino acids, not more than 15, or not more than 11 amino acids in length. Peptides present in or on any one particle are identical to all other peptides on that particle, i.e. the peptides have the same amino acid sequence; other compounds such as lipids, polysaccharides, etc. consist of a single species. The particles may be provided as a group, i.e. a composition or formulation of a plurality of particles with a single antigen species. Alternatively a composition or formulation is provided comprising a cocktail of particles with a plurality of antigen species, with the proviso that each particle contains only a single species of antigen.

Compositions or groups of interest for manufacturing purposes, in kits, and the like may comprise a single antigen species, such as a single peptide species. Compositions and formulations for therapeutic purposes, e.g. for use in a method of treatment, generally include at least two antigen species. Formulations for generating an immune response may include 2, 3, 4, 5, 10, 20, 30, 40, 50 or more antigen species and an equivalent number of groups of particles.

The composition containing the plurality of groups of particles may be a vaccine formulation which may have the particles in a dry form to which a liquid carrier can be added to form a suspension or emulsion, or the liquid carrier may be present and the liquid carrier may be a pharmaceutically acceptable injectable carrier.

The invention also includes a method of treating a subject such as vaccinating a subject whereby a formulation of the invention is injected into an individual in order to elicit an immune response.

The invention also includes a method of making the particles and the population of groups of particles in order to form the formulation.

Formulations used to generate an immune response such as vaccine formulations of the invention can comprise polypeptides that correspond to an epitope, usually a T cell epitope, that, when brought into contact with a mammalian immune system will elicit an immune response to the corresponding epitope on a cell, virus, etc. Epitopes of interest include, without limitation, those present on pathogens, e.g. virus, bacteria, fungi, protozoan, etc.; and may further comprise epitopes associated with, for example, cancer cells. The polypeptides are encapsulated within and/ or bound to the surface of specifically sized particles, where the particles may be formed of any suitable biocompatible material, e.g. biocompatible polymers such as poly(lactic-co-glycolic acid) (PLGA), polycaprolactone, polyglycolide, polylactic acid, poly-3-hydroxybutyrate, etc.

The invention provides optimally sized particles comprised of a biocompatible polymer, wherein the particles are loaded with a population of identical compound species such as identical peptides, where the peptides may correspond to a single epitope, and further wherein the particles are sized so that only a single particle is taken into a single APC at a given point in time.

An aspect of the invention is a composition comprising a first group of particles comprised of a biocompatible polymer and a first chemical species; and a second group of particles comprised of a biocompatible polymer and a second chemical species different from the first chemical species wherein each particle in the first group and the second group is substantially spherical, and has a diameter in a range from 10 microns±20% to 25 microns±20%; or 15 microns±20%.

In another aspect of the invention the first chemical species and second chemical species of the composition consist only of a first peptide and a second peptide consisting only of 8 to 20 amino acids; or 8 to 15 amino acids.

In yet another aspect of the invention the composition further comprises a third, and possibly further additional groups of particles wherein each group is comprised of a biocompatible polymer and a chemical species different from the chemical species within the other groups of particles.

In another aspect of the invention the biocompatible polymer is a polymer selected of the group consisting of poly(lactic-co-glycolic acid) (PLGA), polycaprolactone, polyglycolide, polylactic acid, poly-3-hydroxybutyrate.

Another aspect of the invention is a use of a composition as described here in the manufacture of a formulation for treatment of a patient in order to generate an immune response within the patient.

Another aspect of the invention is a method of treatment which may be a method of generating an immune response in a subject by administering to a subject a formulation as described and disclosed herein and thereafter allowing the formulation to interact with the subject's immune system and thereby generate an immune response.

In another aspect of the invention the formulation is administered by injection.

In yet another aspect of the invention the formulation is administered by contacting the formulation with nasal membranes of the subject such as by the use of a nasal spray, nasal drops, or other formulation designed for administration to and contact with a subject's nasal membrane.

Another aspect of the invention is to provide a process whereby the particles as described above are formed by extrusion from a nozzle in a manner which creates particles and does not damage the antigenic compound, e.g. peptides, etc.

Another aspect of the invention is to provide such a process for producing particles which can be carried out without the use of solvents including organic solvents or any other compounds beyond the biocompatible polymer and chemical species.

Also disclosed is a method of treatment, comprising:
administering to a subject a formulation comprising:
a first group of particles comprising a biocompatible polymer and a first peptide species; and
a second group of particles comprising a biocompatible polymer and a second peptide species different from the first peptide species; and
a third group of peptide particles comprising a biocompatible polymer and a third peptide species different from both the first and second peptide species;
wherein the first, second, and third peptide species consists of 8 to 15 amino acids; and
allowing the groups of particles to interact with the subject's immune system and thereby generate an immune response.

Another aspect on the invention is a method as recited above, wherein the formulation is administered by injection into the subject's lymph system.

Another aspect on the invention is a method as recited above, further comprising:
administering an adjuvant to the subjects.

Another aspect on the invention is a method as recited above, wherein the amino acid sequences comprise epitopes of a pathogen or epitopes on the surface of a cell infected with a pathogen.

Another aspect on the invention is a method as recited above, wherein the pathogen is selected from the group consisting of a virus, a bacteria and a parasite.

Another aspect on the invention is a method as recited above, wherein the administering is by injecting the subject formulation with the formulation.

Another aspect on the invention is a method as recited above, wherein the administering is by contacting nasal membranes of the subject with the formulation.

These and other objects, advantages, and features of the invention will become apparent to those persons skilled in the art upon reading the details of the formulations and methods of treatment as more fully described below.

BRIEF DESCRIPTION OF THE DRAWINGS

FIG. 1 includes four photos (1A, 1B, 10 and 1D). Each of the photos show human dendrocytes and 10 micron diameter particles comprised of PLGA. In FIG. 1A two human dendrocytes are shown in proximity to the microspheres. In FIG. 1B a first human dendrocyte is shown phagocytosing three 10 micron PLGA microspheres with a second dendrocyte beginning phagocytosis. In FIG. 10 the first dendrocyte is shown completing phagocytosis of three 10 micron PLGA microspheres and a second dendrocyte in active phagocytosis. In FIG. 1D the second dendrocyte has completed phagocytosis of three 10 micron PLGA microspheres.

FIG. 2 includes four photos (2A, 2B, 2C and 2D) each of which show human dendrocytes and PLGA microspheres which are 15 microns in diameter. In FIG. 2A two human dendrocytes are in proximity with two 15 micron microspheres. In FIG. 2B a first dendrocyte is phagocytosing a 15 micron microsphere. In FIG. 2C a first dendrocyte has undergone complete phagocytosis of a 15 micron microsphere and a second dendrocyte is in active phagocytosis. In FIG. 2D a second dendrocyte has completed phagocytosis of a single 15 micron microsphere.

These still photos from FIGS. 1 and 2 were taken from videos of human dendrocytes placed in proximity to microspheres wherein the microspheres were 10 microns in diameter for FIG. 1 and 15 microns in diameter for FIG. 2. The photos are part of many taken and were chosen as photos which might best represent aspects of the invention.

DETAILED DESCRIPTION OF THE INVENTION

Before the present composition, formulation and method of manufacture and use and treatment are described, it is to be understood that this invention is not limited to particular embodiment described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

A vaccine is a biological preparation intended to improve a recipient's immunity to a particular disease. A vaccine typically contains an agent that resembles a disease-causing microorganism, and is often made from weakened or killed forms of the microbe or its toxins. The agent stimulates the body's immune system to recognize the agent as foreign, destroy it, and "recognize" it, so that the immune system can more easily recognize and destroy any of these microorganisms that it later encounters. Vaccines can be prophylactic (e.g. to prevent or ameliorate the effects of a future infection by any natural or "wild" pathogen), or therapeutic (e.g. vaccines against cancer are also being investigated).

The expression "enhanced immune response" or similar term means that the immune response is elevated, improved or enhanced to the benefit of the host relative to the prior immune response status, for example, a native status before the administration of an immunogenic composition of the invention.

The terms "cell-mediated immunity" and "cell-mediated immune response" are meant to refer to the immunological defense provided by lymphocytes, such as that defense provided by T cell lymphocytes when they come into close proximity to a target cell. A cell-mediated immune response normally includes lymphocyte proliferation. When "lymphocyte proliferation" is measured, the ability of lymphocytes to proliferate in response to a specific antigen is measured. Lymphocyte proliferation is meant to refer to T-helper cell or cytotoxic T-lymphocyte (CTL) cell proliferation.

The term "immunogenic amount" refers to an amount of antigenic compound sufficient to stimulate an enhanced immune response, when administered with a subject immunogenic composition, as compared with the immune response elicited by the antigen in the absence of the microsphere formulation.

The terms "treatment", "treating", "treat" and the like are used herein to generally refer to obtaining a desired pharmacologic and/or physiologic effect such as an enhanced immune response. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a subject, particularly a mammalian subject, more particularly a human, and includes: (a) preventing the disease or symptom from occurring in a subject which may be predisposed to the disease or symptom but has not yet been diagnosed as having it; (b) inhibiting the disease symptom, e.g., arresting its development; or relieving the disease symptom, i.e., causing regression of the disease or symptom (c) reduction of a level of a product produced by the infectious agent of a disease (e.g., a toxin, an antigen, and the like); and (d) reducing an undesired physiological response to the infectious agent of a disease (e.g., fever, tissue edema, and the like).

The term "antigen presenting cell" or APC may generally refer to a mammalian cell having a surface HLA Class I or HLA Class II molecule in which an antigen is presented. Unless otherwise indicated, for the purposes of the present invention an antigen presenting cell is a "professional" antigen presenting cell that can activate or prime T cells, including naïve T cells. Professional APC usually express both HLA Class I and HLA Class II molecules, and are very efficient at internalizing antigen, either by phagocytosis or by receptor-mediated endocytosis, and then displaying the antigen or a fragment thereof bound to the appropriate HLA molecule on their cell surface. Synthesis of additional co-stimulatory molecules is a defining feature of professional APCs. Of these APCs, dendritic cells (DCs) have the broadest range of antigen presentation, and are the most important T cell activators. Macrophages, B cells and certain activated epithelial cells are also professional APCs.

Invention in General

Formulations of the invention comprise one or a plurality of groups of spherical particles, wherein the particles in each group are identical and further wherein the particles in different groups include a different active ingredient from other groups. The formulation may be designed such that a population of antigen-presenting cells (APC) can be presented with a plurality of antigen species, formulated in such a way that any one antigen presenting cell will take up and present only a limited number of the antigen species, i.e. less than 5, less than 3, usually a single species. There is evidence that presentation of a plurality of epitopes by a single APC may result in immunodominance of a single epitope, which is undesirable in situations where overall responsiveness to the plurality of epitopes is desirable. For example, see Rodriguez, et al., "Immunodominance in Virus-Induced CD8+ T-Cell Responses Is Dramatically Modified by DNA Immunization and Is Regulated by Gamma Interferon" Journal of Virology, 76(9):4251-4259 (May 2002) and Yu et al., "Consistent Patterns in the Development and Immunodominance of Human Immunodeficiency Virus Type I (HIV-1)-Specific CD8+ T-Cell Responses following Acute HIV-1 Infection" Journal of Virology, 76(17):8690-9701 (September 2002), both incorporated herein by reference.

The invention accomplishes the desired result by placing an antigen, for example a peptide antigen as defined herein, on or in a particle of a defined size of a biocompatible polymer, usually in a form that is approved by the United States Food and Drug Administration for administration to humans. Vaccine formulations may be comprised of a pharmaceutically acceptable carrier. The carrier can come in a variety of forms depending on the mode of administration such as injection, nasal, inhalation, oral, etc. In addition to the carrier the formulation includes a plurality of particles which are comprised of a biocompatible polymer and an antigen, e.g. a peptide antigen. The particles may be generally spherical in shape and have a defined diameter in a range of 10 microns to 20 microns±20%, or ±10% or ±5% or ±2%. The diameter of the particles is designed such that an antigen presenting cells such as dendritic cell can consume only a single particle. Each particle may contain a large number of identical compounds, for example peptide species, although the antigen species within any given particle is identical. Thus, each group of particles consist only of copies of one compound, e.g. peptides which have the same amino acid sequence. In some circumstances antigen containing particles may be allowed to include more than a single compound or species, e.g. two, three, four or five compounds, provided that, in the case of peptides, they do not exhibit immunodominance with respect to each other.

Compositions or formulations of the invention are comprised of groups of particles. There may be a plurality of groups which may comprise two or more groups, three or more groups, five or more groups, ten or more groups, twenty or more groups, twenty five or more groups, fifty or more groups, or any desired number of groups. Any group of particles may include a plurality of particles meaning that it may include two or more, three or more, five or more, ten or more, twenty or more, twenty five or more, fifty or more, a hundred or more, a thousand or more particles within any particular group. Further, the number of particles within one group may be the same as or may be different from the number of particles within another group.

Some examples of biocompatible polymers useful in the present invention include hydroxyaliphatic carboxylic acids, either homo- or copolymers, such as poly(lactic acid), poly(glycolic acid), Poly(dl-lactide/glycolide, poly(ethylene glycol); polysaccharides, e.g. lectins, glycosaminoglycans, e.g. chitosan; celluloses, acrylate polymers, and the like. The particle size is selected to (a) be sufficiently small that it is capable of uptake and processing by an antigen presenting cell; and (b) be sufficiently large that an APC will generally take up not more than one particle.

Each set, or group, of particles comprises a single antigen, e.g. peptide species, e.g. peptides of identical sequences. The peptide antigen may be other than a sequence determined to be an immunodominant sequence.

Groups of particles may be combined as a composition or formulation comprising particles with a plurality of peptide species. For example, two groups of particles provide at least two peptide species and larger numbers of groups can provide, at least 3, at least 4, at least 5, at least 10, at least 20, and usually not more than 50, not more than 40, not more than 30 peptide species via corresponding groups of spheres. In one embodiment, all of the particles are substantially spherical and have a diameter in a range of more than 10 microns and less than 20 microns. Each particle is comprised of a biocompatible polymer and with respect to peptides consists only of a single species of peptide, but include a plurality of copies of that single species.

In some embodiments the antigen is embedded in the particle, for example by mixing peptides and polymers prior to formation of the particles. In other embodiments the antigens are coupled to the particle surface. The surface may be optionally textured to simulate, to a degree, the surface of an infectious bacteria, virus or other pathogen.

Particles in a formulation may be heterogenous or homogenous in size, usually homogeneous, where the variability may be not more than 100% of the diameter, not more 50%, not more than 20%, not more than 10%, not more than 2%, etc. Particle sizes are may be about 8 μm in diameter, about 10 μm, about 12 μm about 14 μm, about 15 μm, about 16 μm, about 17, about 18 μm, about 20 μm, not more than about 25 μm diameter.

The optimum size for a particular peptide or class of peptides may be determined empirically by various methods. For example, two different peptides may be detectably labeled with two different fluorophores, and used to prepare particles of the invention. A mixture of the particles is provided to antigen presenting cells, which are then viewed by optical microscope, flow cytometry, etc. to determine if a single fluorophore or if multiple fluorophores are present in any single APC, where the size of particle that provides for exclusive uptake is chosen. Functional tests may also be performed, e.g. by providing particles with the cognate antigens for different T cell lines and determining if one or both lines are activated by an APC.

In order to determine the precise size which is desirable for the particles, various types of labeling can be used. In addition to the fluorophores referred to above, labeling can be performed with semiconductor nanocrystals which are generally referred to as quantum dots. The purpose of carrying out the experiment is to determine a size at which the antigen presenting cells such as the macrophage can consume only a single particle. The size would be too large if the macrophage cannot consume the particle. The size would be too small if the macrophage can consume more than one particle.

The optimum size of particle to achieve the desired result may vary depending on the charge of the peptide that is being presented, for example a positively charged peptide may be more readily ingested by an APC than a neutral or negatively charged peptide. In some embodiments each peptide is individually optimized for a microsphere size that achieves exclusive uptake, and thus a formulation of a plurality of microsphere/peptide combinations may be heterogenous in size, although the size for a peptide species will be narrowly defined.

Based on the above it will be understood that one aspect of the invention is the use of groups of particles of the invention to determine information about the operation of the immune system, particularly with respect to antigen presentation. The groups of particles provide information on how the immune system deals with different antigens in the particles. Thus, the groups of particles of the invention can provide valuable information on how an immune system operates and as such what formulations will provide a desired immune response.

In some embodiments of the invention, a formulation is provided of PLGA microspheres of a defined size from 14 μm to 16 μm in diameter, where each microsphere comprises a single peptide antigen species, and where from 10 to 30 different peptide antigen species are present in the formulation via 10 to 30 different groups of particles. In some embodiments the peptide antigen is an antigen of a virus such as hepatitis C virus (HCV) or human immunodeficiency virus (HIV-1).

Antigen Presenting Cells

The three major classes of antigen presenting cells are dendritic cells (DCs), macrophages, and B cells, but dendritic cells are considerably more potent on a cell-to-cell basis and are the only antigen presenting cells that activate naïve T cells. DC precursors migrate from bone marrow and circulate in the blood to specific sites in the body, where they mature. This trafficking is directed by expression of chemokine receptors and adhesion molecules. Upon exposure to antigen and activation signals, the DCs are activated, and leave tissues to migrate via the afferent lymphatics to the T cell rich paracortex of the draining lymph nodes. The activated DCs then secrete chemokines and cytokines involved in T cell homing and activation, and present processed antigen to T cells. The groups of particles of the invention provide information on how to best present processed antigens to T cells to obtain a desired immune response.

DCs mature by upregulating costimulatory molecules (CD40, CD80 and CD86), and migrate to T cell areas of organized lymphoid tissues where they activate naive T cells and induce effector immune responses. In the absence of such inflammatory or infectious signals, however, DCs present self-antigens in secondary lymphoid tissues for the induction and maintenance of self-tolerance. Dendritic cells include myeloid dendritic cells and plasmacytoid dendritic cells.

For purposes of the invention, e.g. determining the uptake of particles of any formulation including a vaccine formulations by APC, any one of the classes of APC may be used, including without limitation immature DC, monocytes, mature myeloid DC, mature pDC, etc. For example see Foged et al (2005) International Journal of Pharmaceutics 298(2): 315-322; Reece et al. (2001) Immunology and Cell Biology 79:255-263; Tel et al. (2010) J. Immunol. 184:4276-4283, each herein specifically incorporated by reference.

Antigens

The term "antigen" as used herein includes meanings known in the art, and means a molecule or portion of a molecule, frequently for the purposes of the present invention a polypeptide molecule (amino acid sequence), that can react with a recognition site on an antibody or T cell receptor. The term "antigen" also includes a molecule or a portion of a molecule that can, either by itself or in conjunction with an adjuvant or carrier, elicit an immune response (also called an "immunogen"). The groups of particles of the invention provide information on how to best structure antigen components in the particles to increase or decrease an immune response in a desired way.

The "specificity" of an antibody or T cell receptor refers to the ability of the variable region to bind with high affinity to an antigen. The portion of the antigen bound by the immune receptor is referred to as an epitope, and an epitope is that portion of the antigen which is sufficient for high affinity binding. An individual antigen typically contains multiple epitopes, although there are instances in which an antigen contains a single epitope. In some embodiments of the invention, a plurality of peptide fragments representing individual epitopes are derived from a protein antigen. Where the antigen is a peptide, generally a linear epitope will be at least about 8 amino acids in length, and not more than about 15 to 22 amino acids in length. A T cell receptor recognizes a more complex structure than antibodies, and requires both a major histocompatibility antigen binding pocket and an antigenic peptide to be present. The binding affinity of T cell receptors to epitopes is lower than that of antibodies to epitopes, and will usually be at least about $10^{-4}$ M, more usually at least about $10^{-5}$ M.

Antigens of interest for the purposes of the invention include pathogens and portions thereof, e.g. proteins, peptides, polysaccharides, etc., e.g. virus, bacteria, protozoans, etc.; tumor antigens, and the like. Viral pathogens of interest include retroviral pathogens, e.g. HIV-1; HIV-2, HTLV, FIV, SIV, etc.; influenza, smallpox (vaccinia), measles, mumps, rubella, poliovirus, rotavirus, varicella (chickenpox), hepatitis A, B, C, D virus, bacterial antigens, tumor antigens, and the like. Microbes of interest include, but are not limited to the following, include: *Citrobacter* sp.; *Enterobacter* sp.; *Escherichia* sp., e.g. *E. coli; Klebsiella* sp.; *Morganella* sp.; *Proteus* sp.; *Providencia* sp.; *Salmonella* sp., e.g. *S. typhi, S. typhimurium; Serratia* sp.; *Shigella* sp.; *Pseudomonas* sp., e.g. *P. aeruginosa; Yersinia* sp., e.g. *Y. pestis, Y. pseudotuberculosis, Y enterocolitica; Franciscella* sp; *Pasturella* sp.; *Vibrio* sp., e.g. *V. cholerae, V. parahemolyticus; Campylobacter* sp., e.g. *C. jejuni; Haemophilus* sp., e.g. *H. influenzae, H. ducreyi; Bordetella* sp., e.g. *B. pertussis, B. bronchiseptica, B. parapertussis; Brucella* sp., *Neisseria* sp., e.g. *N. gonorrhoeae, N. meningitidis*, etc. Other bacteria of interest include *Legionella* sp., e.g. *L. pneumophila; Listeria* sp., e.g. *L. monocytogenes; Staphylococcus* sp., e.g. *S. aureus Mycoplasma* sp., e.g. *M. hominis, M. pneumoniae; Mycobacterium* sp., e.g. *M. tuberculosis, M. leprae;*

*Treponema* sp., e.g. *T. pallidum*; *Borrelia* sp., e.g. *B. burgdorferi*; *Leptospirae* sp.; *Rickettsia* sp., e.g. *R. rickettsii*, *R. typhi*; *Chlamydia* sp., e.g. *C. trachomatis*, *C. pneumoniae*, *C. psittaci*; *Helicobacter* sp., e.g. *H. pylori*, etc.

Antigenic peptides can include purified native peptides, synthetic peptides, recombinant proteins, crude protein extracts, attenuated or inactivated viruses, cells, microorganisms, or fragments of such peptides. Immunogenic peptides can be native or synthesized chemically or enzymatically. Any method of chemical synthesis known in the art is suitable. Solution phase peptide synthesis can be used to construct peptides of moderate size or, for the chemical construction of peptides, solid phase synthesis can be employed. Atherton et al. (1981) Hoppe Seylers Z. Physiol. Chem. 362:833-839. Proteolytic enzymes can also be utilized to couple amino acids to produce peptides. Kullmann (1987) Enzymatic Peptide Synthesis, CRC Press, Inc. Alternatively, the peptide can be obtained by using the biochemical machinery of a cell, or by isolation from a biological source. Recombinant DNA techniques can be employed for the production of peptides. Hames et al. (1987) Transcription and Translation: A Practical Approach, IRL Press. Peptides can also be isolated using standard techniques such as affinity chromatography.

The groups of particles of the invention can be used to determine which antigens and antigen synthesis techniques result in obtaining an immune response desired.

Type of Vaccines

The groups of particles of the invention can use epitope portions of vaccine materials as described below to determine which positions of these materials obtain the desired immune response. Such information can be used to create safer, less expensive and more effective vaccines.

Some vaccines contain inactivated, but previously virulent, micro-organisms that have been destroyed with chemicals or heat. Examples are the influenza vaccine, cholera vaccine, bubonic plague vaccine, polio vaccine, hepatitis A vaccine, and rabies vaccine. Other vaccines contain live, attenuated microorganisms. Many of these are live viruses that have been cultivated under conditions that disable their virulent properties, or which use closely-related but less dangerous organisms to produce a broad immune response, however some are bacterial in nature. They typically provoke more durable immunological responses and are the preferred type for healthy adults. Examples include the viral diseases yellow fever, measles, rubella, and mumps and the bacterial disease typhoid. The live Mycobacterium tuberculosis vaccine developed by Calmette and Guerin is not made of a contagious strain, but contains a related species called "BCG".

Toxoid vaccines are made from inactivated toxic compounds that cause illness rather than the micro-organism. Examples of toxoid-based vaccines include tetanus and diphtheria. Toxoid vaccines are known for their efficacy. Not all toxoids are for micro-organisms; for example, *Crotalus atrox* toxoid is used to vaccinate dogs against rattlesnake bites.

In subunit vaccine, a fragment of a microorganism is utilized to induce an immune response. Examples include the subunit vaccine against Hepatitis B virus, which is composed of only the surface proteins of the virus (previously extracted from the blood serum of chronically infected patients, but now produced by recombination of the viral genes into yeast); the virus-like particle (VLP) vaccine against human papillomavirus (HPV) that is composed of the viral major capsid protein, and the hemagglutinin and neuraminidase subunits of the influenza virus.

In conjugate vaccines, the polysaccharides present on bacterial outer coats are conjugated to a carrier to induce a more robust response, e.g. in the *Haemophilus influenzae* type B vaccine.

Vaccines currently in development include dendritic cell vaccines, which combine dendritic cells with antigens, which have shown some positive preliminary results for treating brain tumors. In recombinant vector vaccines, the physiology of one micro-organism is combined with the DNA of the other, to create immunity against diseases that have complex infection processes. DNA vaccination, created from an infectious agent's DNA, has been developed. It works by insertion (and expression, triggering immune system recognition) of viral or bacterial DNA into human or animal cells. Some cells of the immune system that recognize the proteins expressed will mount an attack against these proteins and cells expressing them. Because these cells live for a very long time, if the pathogen that normally expresses these proteins is encountered at a later time, they will be attacked instantly by the immune system. One advantage of DNA vaccines is that they are very easy to produce and store. T-cell receptor peptide vaccines are under development for several diseases using models of Valley Fever, stomatitis, and atopic dermatitis. These peptides have been shown to modulate cytokine production and improve cell mediated immunity. Other vaccines are in development to target bacterial proteins that are involved in complement inhibition, which would neutralize a key bacterial virulence mechanism.

While most vaccines are created using inactivated or attenuated compounds from micro-organisms, synthetic vaccines are composed mainly or wholly of synthetic peptides, carbohydrates or antigens.

Vaccines may be monovalent (also called univalent) or multivalent (also called polyvalent). A monovalent vaccine is designed to immunize against a single antigen or single microorganism. A multivalent or polyvalent vaccine is designed to immunize against two or more strains of the same microorganism, or against two or more microorganisms. In certain cases a monovalent vaccine may be preferable for rapidly developing a strong immune response.

In order to provide the best protection against an infection, children are recommended to receive vaccinations as soon as their immune systems are sufficiently developed to respond to particular vaccines, with additional "booster" shots often required to achieve "full immunity". This has led to the development of complex vaccination schedules. In the United States, the Advisory Committee on Immunization Practices, which recommends schedule additions for the Centers for Disease Control and Prevention, recommends routine vaccination of children against: hepatitis A, hepatitis B, polio, mumps, measles, rubella, diphtheria, pertussis, tetanus, HiB, chickenpox, rotavirus, influenza, meningococcal disease and pneumonia. The large number of vaccines and boosters recommended (up to 24 injections by age two) has led to problems with achieving full compliance. In order to combat declining compliance rates, various notification systems have been instituted and a number of combination injections are now marketed (e.g., Pneumococcal conjugate vaccine and MMRV vaccine), which provide protection against multiple diseases.

Besides recommendations for infant vaccinations and boosters, many specific vaccines are recommended at other ages or for repeated injections throughout life—most commonly for measles, tetanus, influenza, and pneumonia. Pregnant women are often screened for continued resistance to rubella. The human papillomavirus vaccine is currently recommended in the U.S. and UK for ages 11-25. Vaccine recommendations for the elderly concentrate on pneumonia and influenza, which are more deadly to that group. In 2006, a vaccine was introduced against shingles, a disease caused by the chickenpox virus, which usually affects the elderly.

Use of groups of particles of the invention can provide information that will allow for the reformulation of current vaccines, e.g. reducing undesired immune responses via small antigen components, improving patient compliance by obtaining an immune response that does not require a follow-up booster. Information obtained via the groups of particles of the invention can also be combined with patient specific HLA information to tailor immunogens to specific groups of HLA types.

Producing Particles of the Formulation

Particles of the formulation can be produced in a number of different ways. However, it is desirable that the particles be produced with certain specific characteristics. For example, it is desirable that the particles in a formulation all have the same size±20%, ±10%, ±5%, ±2%. It is also desirable that the process for producing the particles produce the particles without damaging the peptides of epitopes on the attenuated viruses in the particles. Such particles can be produced using a process referred to as "Flow Focusing" as disclosed within U.S. Pat. No. 6,116,516 issued Sep. 12, 2000 to Alfonso Ganan-Calvo, herein incorporated by reference.

Substantially any biocompatible polymer can be used in forming the particles. Those skilled in the art will appreciate that polymers can be selected from the group consisting of poly(lactic-co-glycolic acid) (PLGA), polycaprolactone, polyglycolide, polylactic acid, poly-3-hydroxybutyrate. Different polymer and different degree of polymerization and cross-linking can be used to obtain a desired release profile of the particles contents.

With respect to the peptide, the amino acid sequence in any given group of particles will be identical and will be chosen based on the particular pathogen of interest. Identical peptide sequences are produced and mixed with the desired polymer such as PLGA and the polymer with the peptides is extruded from a device (as disclosed within U.S. Pat. No. 6,116,516 which is incorporated herein by reference in its entirety) to produce particles.

In the present invention the epitope may consist only of an amino acid sequence, which could be produced from a virus. Viruses are grown either on primary cells such as chicken eggs (e.g., for influenza), or on continuous cell lines such as cultured human cells (e.g., for hepatitis A). Bacteria are grown in bioreactors (e.g., *Haemophilus influenzae* type b). Alternatively, a recombinant protein derived from the viruses or bacteria can be generated in yeast, bacteria, or cell cultures. After the antigen is generated, it is isolated from the cells used to generate it. A virus may need to be inactivated, possibly with no further purification required. Recombinant proteins need many operations involving ultrafiltration and column chromatography.

The vaccine may be formulated by adding adjuvant, stabilizers, and preservatives as needed to water, saline solution or other flowable liquid. The adjuvant enhances the immune response of the antigen, stabilizers increase the storage life, and preservatives allow the use of multidose vials. Combination vaccines are harder to develop and produce, because of potential incompatibilities and interactions among the antigens and other ingredients involved.

Vaccine production techniques are evolving. Cultured mammalian cells are expected to become increasingly important, compared to conventional options such as chicken eggs, due to greater productivity and few problems with contamination. Recombination technology that produces genetically detoxified vaccine is expected to grow in popularity for the production of bacterial vaccines that use toxoids. Combination vaccines are expected to reduce the quantities of antigens they contain, and thereby decrease undesirable interactions, by using pathogen-associated molecular patterns. Groups of particles of the invention can be used to provide combination vaccines.

Formulations

The compositions of the invention are especially useful for administration to an individual in need of immune stimulation (in the context of, for example, infectious disease, cancer, and allergy), and generally comprise a plurality of groups of microspheres of defined size comprising distinct antigen species as described herein, in a sufficient amount to modulate an immune response.

The compositions of the invention optionally comprise a pharmaceutically acceptable excipient, and may be in various formulations. As is well known in the art, a pharmaceutically acceptable excipient is a relatively inert substance that facilitates administration of a pharmacologically effective substance. For example, an excipient can provide form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and non-parenteral drug delivery are set forth in Remington's Pharmaceutical Sciences 19th Ed. Mack Publishing (1995).

Generally, these compositions are formulated for administration by injection or inhalation, e.g., intraperitoneally, intravenously, subcutaneously, intramuscularly, etc. Accordingly, these compositions are preferably combined with pharmaceutically acceptable vehicles such as saline, Ringer's solution, dextrose solution, and the like. The particular dosage regimen, i.e., dose, timing and repetition, will depend on the particular individual and that individual's medical history.

In some embodiments, more than one antigen(s) may be present in a composition. Compositions or formulations of the invention may be liquid dispersions where the carrier liquid is water and groups of particles provide the dispersion. A plurality of groups can provide at least two peptide species, at least 3, at least 4, at least 5, at least 10, at least 20, and usually not more than 50, not more than 40, not more than 30 peptide species. Such "cocktails", as they are often denoted in the art, may be particularly useful in immunizing against pathogens present in different variants, e.g. HIV, rotavirus, influenza, etc. Alternatively, such formulations can provide information on developing a vaccine.

Generally, the efficacy of administering any of these compositions is adjusted by measuring any change in the immune response as described herein, or other clinical parameters.

In some embodiments, the invention provides compositions comprising polypeptides as described herein and an adjuvant whereby the polypeptide(s)/adjuvant are co-administered. The immunogenic composition may contain an amount of an adjuvant sufficient to potentiate the immune response to the immunogen. Adjuvants are known in the art and include, but are not limited to, oil-in-water emulsions, water-in oil emulsions, alum (aluminum salts), liposomes and microparticles including but not limited to, polystyrene, starch, polyphosphazene and polylactide/polyglycosides.

Other suitable adjuvants also include, but are not limited to, MF59, DETOX™ (Ribi), squalene mixtures (SAF-1), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) Nature 344:873-875, as well as, lipid-based adjuvants and others described herein. For veterinary use and for production of antibodies in animals, mitogenic components of Freund's adjuvant (both complete and incomplete) can be used.

In some embodiments, the plurality of groups of microspheres or particles of defined size comprising distinct antigen species described herein can be administered in conjunction with one or more immunomodulatory facilitators. Thus, the invention provides compositions comprising plurality of microspheres of defined size comprising distinct antigen species and an immunomodulatory facilitator. As used herein, the term "immunomodulatory facilitator" refers to molecules which support and/or enhance immunomodulatory activity. Immunomodulatory facilitators include, but are not limited to, co-stimulatory molecules (such as cytokines, chemokines, targeting protein ligand, trans-activating factors, peptides, and peptides comprising a modified amino acid) and adjuvants (such as alum, lipid emulsions, and polylactide/polyglycolide microparticles).

The following excipients are commonly present in compositions to generate an immune response such as vaccine preparations. Aluminum salts or gels are added as adjuvants. Adjuvants are added to promote an earlier, more potent response, and more persistent immune response to the vaccine; they allow for a lower vaccine dosage. Antibiotics are added to some vaccines to prevent the growth of bacteria during production and storage of the vaccine. Egg protein is present in influenza and yellow fever vaccines as they are prepared using chicken eggs. Other proteins may be present. Formaldehyde is used to inactivate bacterial products for toxoid vaccines. Formaldehyde is also used to kill unwanted viruses and bacteria that might contaminate the vaccine during production. Monosodium glutamate (MSG) and 2-phenoxyethanol are used as stabilizers in a few vaccines to help the vaccine remain unchanged when the vaccine is exposed to heat, light, acidity, or humidity. Thimerosal is a mercury-containing preservative that is added to vials of vaccine that contain more than one dose to prevent contamination and growth of potentially harmful bacteria.

Many vaccines need preservatives to prevent serious adverse effects. Several preservatives are available, including thiomersal, phenoxyethanol, and formaldehyde. Thiomersal is more effective against bacteria, has better shelf life, and improves vaccine stability, potency, and safety, but in the U.S., the European Union, and a few other affluent countries, it is no longer used as a preservative in childhood vaccines, as a precautionary measure due to its mercury content. Although controversial claims have been made that thiomersal contributes to autism, no convincing scientific evidence supports these claims.

Administration and Assessment of the Immune Response

The plurality of groups of microspheres or particles of the invention of defined size, where each group of particles defines a distinct antigen species composition can be administered in combination with other pharmaceutical and/or immunogenic and/or immunostimulatory agents and can be combined with a physiologically acceptable carrier thereof.

As with all immunogenic compositions, the immunologically effective amounts and method of administration of the particular formulation can vary based on the individual, what condition is to be treated and other factors evident to one skilled in the art. Factors to be considered include the antigenicity, route of administration and the number of immunizing doses to be administered. Such factors are known in the art and it is well within the skill of immunologists to make such determinations without undue experimentation. A suitable dosage range is one that provides the desired modulation of immune response to the antigen. Generally, a dosage range may be, for example, from about any of the following, referencing the amount of peptide in a dose exclusive of carrier: 0.01 to 100 µg, 0.01 to 50 µg, 0.01 to 25 µg, 0.01 to 10 µg, 1 to 500 µg, 100 to 400 µg, 200 to 300 µg, 1 to 100 µg, 100 to 200 µg, 300 to 400 µg, 400 to 500 µg. Alternatively, the doses can be about any of the following: 0.1 µg, 0.25 µg, 0.5 µg, 1.0 µg, 2.0 µg, 5.0 µg, 10 µg, 25 µg, 50 µg, 75 µg, 100 µg. Accordingly, dose ranges can be those with a lower limit about any of the following: 0.1 µg, 0.25 µg, 0.5 µg and 1.0 µg; and with an upper limit of about any of the following: 250 µg, 500 µg and 1000 µg. The absolute amount given to each patient depends on pharmacological properties such as bioavailability, clearance rate and route of administration.

The effective amount and method of administration of the particular formulation can vary based on the individual patient and other factors evident to one skilled in the art. Routes of administration include but are not limited to all types of injection including IV and IM, topical, dermal, transdermal, transmucosal, nasal, oral, epidermal, parenteral, gastrointestinal, and naso-pharyngeal and pulmonary, including transbronchial and transalveolar. The absolute amount given to each patient depends on pharmacological properties such as bioavailability, clearance rate and route of administration.

Parenteral routes of administration include but are not limited to electrical (iontophoresis) or direct injection such as direct injection into a central venous line, intravenous, intramuscular, intraperitoneal, intradermal, or subcutaneous injection. Compositions suitable for parenteral administration include, but are not limited, to pharmaceutically acceptable sterile isotonic solutions. Such solutions include, but are not limited to, saline and phosphate buffered saline for injection of the compositions.

Naso-pharyngeal and pulmonary routes of administration include, but are not limited to, inhalation, transbronchial and transalveolar routes. The invention includes compositions suitable for administration by inhalation including, but not limited to, various types of aerosols for inhalation, as well as powder forms for delivery systems. Devices suitable for administration by inhalation of include, but are not limited to, atomizers and vaporizers. Atomizers and vaporizers filled with the powders are among a variety of devices suitable for use in inhalation delivery of powders.

The methods of producing suitable devices for injection, topical application, atomizers and vaporizers are known in the art and will not be described in detail.

The above-mentioned compositions and methods of administration are meant to describe but not limit the methods of administering the compositions of the invention.

The methods of producing the various compositions and devices are within the ability of one skilled in the art and are not described in detail here.

Analysis (both qualitative and quantitative) of the immune response to the subject compositions can be by any method known in the art, including, but not limited to, measuring antigen-specific antibody production (including measuring specific antibody subclasses), activation of specific populations of lymphocytes such as CD4+ T cells or NK cells, production of cytokines such as IFNγ, IL-2, IL-4, IL-5, IL-10 or IL-12 and/or release of histamine. Methods for measuring specific antibody responses include enzyme-linked immunosorbent assay (ELISA) and are well known in the art. Measurement of numbers of specific types of lymphocytes such as CD4+ T cells can be achieved, for example, with fluorescence-activated cell sorting (FACS). Serum concentrations of cytokines can be measured, for example, by ELISA. These and other assays to evaluate the immune response to an immunogen are well known in the art. See, for example, Selected Methods in Cellular Immunology (1980) Mishell and Shiigi, eds., W.H. Freeman and Co.

In some instances, a Th1 or Th2-type response is stimulated, i.e., elicited and/or enhanced. With reference to the invention, stimulating a Th1 or Th2-type immune response can be determined in vitro or ex vivo by measuring cytokine production from cells treated with a composition of the invention as compared to those treated with a conventional vaccine. Methods to determine the cytokine production of cells include those methods described herein and any known in the art. The type of cytokines produced in response to treatment indicates a Th1-type or a Th2-type biased immune response by the cells. As used herein, the term "Th1-type biased" cytokine production refers to the measurable increased production of cytokines associated with a Th1-type immune response in the presence of a stimulator as compared to production of such cytokines in the absence of stimulation. Examples of such Th1-type biased cytokines include, but are not limited to, IL-2, IL-12, and IFNγ. In contrast, "Th2-type biased cytokines" refers to those associated with a Th2-type immune response, and include, but are not limited to, IL-4, IL-5, and IL-13. Cells useful for the determination of activity include cells of the immune system, primary cells isolated from a host and/or cell lines, usually APCs and lymphocytes.

Delivery Systems

There are several new delivery systems in development to make vaccine delivery more efficient. Methods include liposomes and ISCOM (immune stimulating complex). Other vaccine delivery technologies have resulted in oral vaccines. A polio vaccine was developed and tested by volunteer vaccinations with no formal training; the results were positive in that the ease of the vaccines increased dramatically. With an oral vaccine, there is no risk of blood contamination. Oral vaccines are likely to be solid which have proven to be more stable and less likely to freeze; this stability reduces the need for a "cold chain": the resources required to keep vaccines within a restricted temperature range from the manufacturing stage to the point of administration, which, in turn, will decrease costs of vaccines.

A microneedle approach may be used, where the microneedle, which is "pointed projections fabricated into arrays that can create vaccine delivery pathways through the skin". Microneedles (MN), as used herein, refers to an array comprising a plurality of micro-projections, generally ranging from about 25 to about 2000 μm in length, which are attached to a base support. An array may comprise $10^2$, $10^3$, $10^4$, $10^5$ or more microneedles, and may range in area from about 0.1 cm$^2$ to about 100 cm$^2$. Application of MN arrays to biological membranes creates transport pathways of micron dimensions, which readily permit transport of macromolecules such as large polypeptides. The microneedle array may be formulated as a transdermal drug delivery patch. MN arrays can alternatively be integrated within an applicator device which, upon activation, can deliver the MN array into the skin surface, or the MN arrays can be applied to the skin and the device then activated to push the MN through the skin.

Methods of the Invention

The invention also includes methods of modulating an immune response comprising administering an immunogenic formulation as described herein to an individual in an amount sufficient to modulate the immune response. Generally, the individual is in need of, or will be in need of, such modulation, due, for example, for a disease condition or being at risk of developing a disease condition. Examples of disease conditions include, but are not limited to, allergy, cancer, infectious diseases (such as viral or bacterial infection).

Methods of the invention include manufacturing particles of a biocompatible polymer having individual chemical species within the particle and then manufacturing groups of particles to create formulations and using those formulations to modulate an immune response within a subject, or, alternatively, using those formulations to study the immune system of a subject to obtain information in the development of a formulation to modulate an immune response in a subject.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

In Example 1 10 micron diameter spherical particles 3, 3', 3", etc. comprised of poly(lactic-co-glycolic acid) (PLGA) are used. The particles had substantially the same diameter±10% or less. The particles were placed in a solution containing human dendrocytes 1 and 2. Photos were taken of the cells prior to (FIG. 1A), during (FIG. 1B) and (FIG. 1C) and after (FIG. 1D) the cells 1 and 2 consumed the particles. The particles 3, 3', 3", etc. were produced using a process as described within U.S. Pat. No. 6,116,516.

Example 2

In Example 1 15 micron diameter spherical particles 3, 3', 3", etc. comprised of poly(lactic-co-glycolic acid) (PLGA)

are used. The particles had substantially the same diameter±10% or less. The particles were placed in a solution containing human dendrocytes 1 and 2. Photos were taken of the cells prior to (FIG. 2A), during (FIG. 2B) and (FIG. 2C) and after (FIG. 2D) the cells 1 and 2 consumed the particles. The particles 3, 3', 3", etc. were produced using a process as described within U.S. Pat. No. 6,116,516.

Examples 1 and 2 show how groups of particles can be administered (placed in contact with dendrocytes) and used to determine the size of particles which the dendrocytes of the immune system readily consume. The results of Examples 1 and 2 indicate that for these dendrocytes, particles which are 10 microns in diameter are sufficiently small that multiple particles can be consumed by a single dendrocyte. The 15 micron particles of Example 2 indicate that, for these dendrocytes, only a single particle of 15 microns in diameter can be consumed. Thus, these two Examples indicate, for these dendrocytes, that the particles with a diameter of 15 microns can be used to present a single chemical species, and thereby reduce or eliminate immunodominance issues which might be created when multiple species are simultaneously presented by dendrocytes.

The formula for the volume of a sphere is $(4/3) \times pi \times (radius)^3$. The radius of the 10 micron sphere is 5 and $5^3$ is 125. The radius of the 15 microspheres is 7.5 and $7.5^3$ is 421.815. Thus, a relatively small increase in the diameter of a sphere makes a large increase in the volume of the sphere. The sphere volume is important in terms of the size of the particle that can undergo dendrocyte phagocytosis.

Example 3

Synthesis of antigen containing microspheres. Microspheres of defined size, and containing a single peptide species were synthesized.

| Reagent Name | Supplier | Cat. No. | Purity |
|---|---|---|---|
| Resomer 502H | Boehringer Mannheim | 502H | 99% |
| D-(+)-Mannose | Sigma | M6020 | 98% |
| CMV pp65 peptide* | American Peptide | 305264 | 95% |
| Phosphate-buffered saline (PBS) | Sigma | D8537 | 100% |
| Acetone | Sigma | 270725 | ≥99.9% |

*Note:
Any peptide may be used in the synthesis.

CMV pp65 peptide was solubilized in PBS at 25 mg/ml (hereafter Reagent A; stored at 4 C). Mannose was solubilized in PBS at 200 mgs+400 uL PBS (hereafter Reagent B; stored at room temperature).

For 5 mls of formulation: a) Place 200 mgs of Resomer 502H in glass vial; b) Add 5.0 mL acetone and mix by rocking until Resomer is completely solubilized; c) Place vial in sonicator; d) During sonication, add 80 uL of Reagent A slowly, drop-wise; e) During sonication, add 20 uL of Reagent B slowly, drop-wise; f) Cap vial tightly and continue to sonicate.

The microspheres were formulated for use in cell cultures by suspension in appropriate culture medium. For use in pharmaceutical formulations the culture medium may be substituted with an appropriate excipient, e.g. normal saline, PBS, and the like.

In such formulations, 1 mg of the antigen containing microspheres is resuspended at a concentration (w/v) equal to 1 milligram/100 microliters in sterile tissue culture medium, and mixed well before use by flicking or sonication. The microspheres will settle within minutes so they must be re-mixed directly before using.

For phagocytosis experiments, 10 μl of resuspended microspheres were added to each well of as 24 well plate. In a 96 well plate, 2 μt of resuspended microspheres are used.

Example 4

Assessment of Antigen Presentation

Preparation of Dendritic Cells from peripheral blood mononuclear cells (PBMC). Frozen PBMC cells were obtained from Cellular Technology Limited, from volunteer donors known to have been exposed to CMV, and to be HLA-A02. The volunteer's antigen presenting cells were known to be capable of presenting HCMV pp65 (NLVPMVATV) CMV epitope to T lymphocytes. Human PBMC (Peripheral Blood Mononuclear Cells) isolated from leukopacks and frozen in serum-free CTL-Cryo™ medium. These leukopacks were ethically collected from healthy donors tested for: HBsAg, HBcAb, HCV, HTLV I/II, and STS by serology; as well as HIV I, HCV, and WNV by NAT.

Cells were thawed and plated at a concentration of $1 \times 10^5$ monocytes/well of a 24-well plate in medium supplemented with GM-CSF at a final concentration of 50 ng/ml and IL-4 at a final concentration of 100 ng/ml. Cells were maintained in culture at 37° C./5% $CO_2$ for 6 days; and used with 8 days after that point. Optical microscopy confirmed maturation of monocytes to dendrocytes capable of phagocytosis of 15 micron PLGA microspheres.

Presentation of antigen and stimulation of T cells was assessed by production of human γ-IFN, measured by ELISA. Mature dendrocytes were mixed with T-Lymphocytes and incubated for two hours with either free, soluble NLVPMVATV (at $10^{-9}$ M concentration) or 15 micron PLGA microspheres containing approximately 2% NLVPMVATV, prepared as described in Example 3. Production of γ-IFN was measured after 2 hours. The results are as shown in Table 1, demonstrating that 15 micron microspheres provide antigen that can be taken up by dendritic cells and presented to T cells.

TABLE 1

| Material Added To Cell Prep | ELISA Optical Density |
|---|---|
| Unstimulated Cells (no material added) | 0.055 |
| Incubated with free peptide | 0.612 |
| incubated with microspheres | 0.560 |

It is to be understood that this invention is not limited to the particular methodology, protocols, peptides, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the reagents, cells, constructs, and methodologies that are described in the publications, and which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A composition, comprising:
   a pharmaceutically acceptable carrier;
   a first group of particles comprising a biocompatible polymer, and a first antigen consisting only of a single species consisting of eight to twenty amino acids embedded in the polymer;
   a second group of particles comprising a biocompatible polymer, and a second antigen consisting only of a single species consisting of eight to twenty amino acids embedded in the polymer, the second antigen being different from the first antigen; and
   a third group of particles comprising a biocompatible polymer, and a third antigen consisting only of a single species consisting of eight to twenty amino acids embedded in the polymer, the third antigen being different from both the first and second antigen;
   wherein each particle in the first group, the second group and the third group is substantially spherical, and each particle has a diameter in a range from 10 microns±20% to 25 microns±20%, wherein the particle diameter is such that only a single particle can be consumed by an antigen presenting cell.

2. The composition of claim 1, wherein the biocompatible polymer is selected from the group consisting of poly(lactic-co-glycolic acid) (PLGA), polycaprolactone, polyglycolide, polylactic acid, poly-3-hydroxybutyrate.

3. The composition of claim 1, further comprising:
   a plurality of additional groups of particles with a diameter of from 10 microns±20% to 25 microns±20% and a diameter such that only a single particle can be consumed by an antigen presenting cell wherein additional antigens in each additional group are embedded in the polymer and are different from antigen in all other groups and the antigens of each group consisting only of a single species.

4. The composition of claim 3, wherein all the particles of the composition are 12 microns to 22 microns in diameter±20%.

5. The composition of claim 1, further comprising monophosphoryl lipid A.

6. The composition as claimed in claim 5 wherein the monophosphoryl lipid A is in the pharmaceutically acceptable carrier.

7. A composition, comprising:
   a pharmaceutically acceptable carrier;
   a first group of particles comprising a biocompatible polymer, and a first antigen consisting only of a single species embedded in the polymer;
   a second group of particles comprising a biocompatible polymer, and a second antigen consisting only of a single species embedded in the polymer, the second antigen being different from the first antigen; and
   a third group of particles comprising a biocompatible polymer, and a third antigen consisting only of a single species embedded in the polymer, the third antigen species being different from both the first and second antigen species,
   wherein each particle in the first group, second group and third group is substantially spherical, and each particle has a diameter in a range of from 10 microns±20% to 25 microns±20%, wherein the particle diameter is such that only a single particle can be consumed by an antigen presenting cell, and wherein the biocompatible polymer is selected from the group consisting of poly (lactic-co-glycolic acid) (PLGA), polycaprolactone, polyglycolide, polylactic acid, poly-3-hydroxybutyrate,
   wherein the first, second and third antigens are each different antigens consisting of eight to twenty amino acids.

8. The composition of claim 7, further comprising:
   a plurality of additional groups of particles with a diameter of from 10 microns±20% to 25 microns±20% and a diameter such that only a single particle can be consumed by an antigen presenting cell wherein additional antigens in each additional group are embedded in the polymer and are different from the antigens in all other groups.

9. The composition of claim 7, further comprising monophosphoryl lipid A.

10. The composition as claimed in claim 9 wherein the monophosphoryl lipid A is in the pharmaceutically acceptable carrier.

11. The composition of claim 8, wherein all the particles of the composition are 12 microns to 22 microns in diameter±20%.

12. The composition of claim 8, wherein all the particles of the composition are 13 microns to 17 microns in diameter±20%.

13. A composition, comprising:
   a pharmaceutically acceptable carrier;
   a first group of particles comprising a biocompatible polymer, and a first antigen consisting only of a single species consisting of eight to twenty amino acids embedded in the polymer; and
   a second group of particles comprising a biocompatible polymer, and a second antigen consisting only of a single species consisting of eight to twenty amino acids embedded in the polymer, the second antigen being different from the first antigen;
   a plurality of additional groups of particles with a diameter such that only a single particle can be consumed by an antigen presenting cell wherein additional antigens in each additional group are embedded in the polymer and are different from antigen in all other groups and the antigens of each group consisting only of a single species;

wherein each particle in the first group, the second group, and the additional groups, the diameter being substantially spherical, and has a diameter such that only a single particle can be consumed by an antigen presenting cell, the particle diameter being in a range of from 10 microns±20% to 25 microns±20%;

wherein the biocompatible polymer is selected from the group consisting of poly(lactic-co-glycolic acid) (PLGA), polycaprolactone, polyglycolide, polylactic acid, poly-3-hydroxybutyrate.

14. The composition of claim 13, further comprising monophosphoryl lipid A.

15. The composition as claimed in claim 14 wherein the monophosphoryl lipid A is in the pharmaceutically acceptable carrier.

16. A vaccine composition, comprising:
a pharmaceutically acceptable carrier;
a first group of particles comprising a biocompatible polymer, and a first antigen consisting only of a single species consisting of eight to twenty amino acids embedded in the polymer;
a second group of particles comprising a biocompatible polymer, and a second antigen consisting only of a single species consisting of eight to twenty amino acids embedded in the polymer, the second antigen being different from the first antigen; and
a third group of particles comprising a biocompatible polymer, and a third antigen consisting only of a single species consisting of eight to twenty amino acids embedded in the polymer, the third antigen being different from both the first and second antigen;
wherein each particle in the first group, the second group and the third group is substantially spherical, and each particle has a diameter in a range from 10 microns±10% to 15 microns±10%, wherein the particle diameter is such that only a single particle can be consumed by an antigen presenting cell.

17. The vaccine composition of claim 16, wherein the biocompatible polymer is selected from the group consisting of poly(lactic-co-glycolic acid) (PLGA), polycaprolactone, polyglycolide, polylactic acid, poly-3-hydroxybutyrate.

18. The vaccine composition of claim 16, further comprising:
a plurality of additional groups of particles with a diameter of from 10 microns±10% to 20 microns±10% and a diameter such that only a single particle can be consumed by an antigen presenting cell wherein additional antigens in each additional group are embedded in the polymer and are different from antigen in all other groups and the antigens of each group consisting only of a single species.

19. The vaccine composition of claim 16, further comprising monophosphoryl lipid A.

20. The vaccine composition as claimed in claim 19 wherein the monophosphoryl lipid A is in the pharmaceutically acceptable carrier.

* * * * *